United States Patent [19]

Matsui et al.

[11] Patent Number: 5,379,110
[45] Date of Patent: * Jan. 3, 1995

[54] METHOD AND APPARATUS FOR MEASURING SURFACE CHARACTERISTICS OF MATERIAL

[75] Inventors: Toshiaki Matsui, Tokyo; Kenichi Araki, Higashi-Murayama, both of Japan

[73] Assignee: Communications Research Laboratory, Ministry of Posts and Telecommunications, Tokyo, Japan

[*] Notice: The portion of the term of this patent subsequent to Apr. 30, 2008 has been disclaimed.

[21] Appl. No.: 965,856

[22] Filed: Oct. 23, 1992

[30] Foreign Application Priority Data

Oct. 23, 1991 [JP] Japan .................................. 3-339277

[51] Int. Cl.$^6$ ............................................ G01N 21/55
[52] U.S. Cl. .................................... 356/445; 356/352; 505/842
[58] Field of Search ................ 356/445, 352; 333/227, 333/230; 505/842

[56] References Cited

U.S. PATENT DOCUMENTS 5,012,212  4/1991  Matsui et al. .

OTHER PUBLICATIONS

The 13th International Conference on Infrared and Millimeter Waves, Dec. 5-9, 1988, 2 pages, T. Matsui, et al., "An Open Resonator for Testing Surface Resistivity of Superconductor Films & Metallic Samples at 100-120 GHz".

*Primary Examiner*—Vincent P. McGraw
*Assistant Examiner*—LaCharles Keesee
*Attorney, Agent, or Firm*—Oblon, Spivak, McClelland, Maier & Neustadt

[57] ABSTRACT

The surface characteristics with respect to a high-frequency electromagnetic field of a material to be tested are measured by placing opposite a flat mirror material to be tested one of a pair of concave spherical reflection mirrors fabricated in the same way and formed with high-reflectance circular coupling regions, placing the other spherical reflection mirror at a position symmetrical to the one reflection mirror with respect to the flat mirror material as the plane of symmetry, measuring the Q value of the open resonator formed by the one reflection mirror and the flat mirror material, removing the flat mirror material from the optical axis, measuring the Q value of the open resonator formed by the pair of spherical reflection mirrors, calculating the absolute value of the reflectance of the flat mirror material to be tested from the difference between the two measured Q values, and calculating the phase of the reflected wave at the surface of the flat mirror material to be tested from the measured resonance position.

9 Claims, 5 Drawing Sheets

METHOD AND APPARATUS FOR MEASURING SURFACE CHARACTERISTICS OF MATERIAL

BACKGROUND OF THE INVENTION

Field of the Invention

This invention relates to a method and an apparatus for measuring the surface characteristics of a material, more particularly to a method and an apparatus for detecting, with high sensitivity, extremely small reflection loss occurring at the surface of a highly conductive material, a superconductor, a ferromagnetic material, any of various thin film materials, a laminated dielectric film or other such material exhibiting a high reflectivity of nearly 100% with respect to impinging electromagnetic waves in the microwave-submillimeter wave band, thus enabling high-precision measurement and evaluation of the surface state of the material in high-frequency electromagnetic fields.

Prior Art Statement

High-precision measurement of the surface reflection characteristics exhibited in the microwave-millimeter wave band by metals, superconductors and other materials is important in such areas as basic material research and the evaluation of material function required in ultra-high frequency technology applications.

In the far-infrared-millimeter wave band, the reflection spectral characteristics of mirror-finished materials are measured by a spectroscopic method using monochromatic light obtained using a diffraction grating. A thin film of gold or aluminum is generally used as the reference mirror surface, and the surface reflectance of the material being tested is calibrated by comparing the reflection intensity from the reference mirror surface with the reflection intensity from the material being tested.

Fourier transform spectroscopy also plays an important role in the same wavelength band. It uses a wavelength band extracted from the wideband black body radiation emitted by a high-pressure mercury lamp directly, without spectral diffraction. The reflection spectral characteristics of a specimen mirror surface are determined by causing light reflected from the specimen to interfere with light reflected from another mirror surface, and computer processing the result.

Such spectroscopic methods are appropriate for measuring the wavelength dependence of surface reflectance which varies greatly in the vicinity of the superconductivity energy gap. One of its drawbacks is that the weak light source used generally makes it nearly impossible to secure a S/N ratio at wavelengths of 2-3 mm. Another is its inability to detect the slight variations in surface reflectance that occur at the surface of a high reflectance material.

High-sensitivity detection of very slight differences in reflectivity between high-reflectance specimens of the same type and of very minute variations in surface reflectivity of the same specimen requires a measurement method which uses a resonator for repeatedly producing interactions between the high-frequency electromagnetic field and the surface of the material being tested. The main technologies for employing a resonator in the measurement of surface characteristics are summarized in the following paragraphs.

Techniques for high-precision measurement of the high-frequency surface impedance of superconductors are of interest as regards research into the superconductivity energy gap, the penetration depth of magnetic field and other physical properties, and are also highly important in the development of materials for use in, for example, high-performance device technologies that capitalize on ultra-low loss characteristics in the ultra-high frequency range. Ever since the discovery of the oxide high-temperature superconductors, measurement of surface impedance has been conducted in parallel with the efforts to develop new superconducting materials of this type. The transmission-type hollow cylindrical resonators commonly used in measuring the surface impedance of high-temperature superconductors are illustrated schematically in FIG. 1 and, in each, one end plate of the hollow cylindrical resonator 51 has a hollow resonator coupling region 55 constituted by two small coupling holes and the coupling holes are respectively connected by transmission line 56 to a driving signal source and a signal detector (neither shown). FIG. 1($a$) shows a configuration in which resonance characteristics are measured by interchanging the other end plate of the hollow cylindrical resonator 51 between a metal (e.g. copper) mirror surface 52 and a test mirror specimen 53, for example, a superconductor. FIG. 1($b$) shows a configuration for use when a large-area test specimen cannot be obtained, in which the test specimen 54 is placed on a substrate 57 and analysis is conducted by the perturbation method. Measurements using the aforesaid hollow cylindrical resonator are generally conducted in the TE011 mode. This is because this mode has a higher Q value than other modes and also because the fact that the electric field is symmetrical relative to the cylinder axis and is directed solely in the circumferential direction means that no current passes through the joint between the cylindrical end plate portions, so that variations in the electrical properties of the end plate joint do not affect the resonator Q value, which is convenient from the point of comparative measurement.

If the measured Q value and the resonant frequency when the reference metal mirror surface is used as the end plate of the hollow cylindrical resonator are defined as Qr and fr, and if the measured Q value and the resonant frequency when the end plate is then replaced with the test specimen are defined as Qs and fs, the surface impedance $Zs(=Rs+jXs)$ can be obtained as a relative value from the variation in the measurement results. More specifically, the difference $\Delta[1/Q]$ between the reciprocals of the measured Q values $(=1/Qs-1/Qr)$ and the difference $\Delta f$ between the resonant frequencies $(=fs-fr)$ are proportional to the difference in impedance $\Delta Zs$ between the specimen and the reference metal mirror surface $(=\Delta Rx+j\Delta Xs)$. Thus by multiplying by the constant $\gamma$ for the resonator and the specimen, we get $\Delta[1/Q]-2j[\Delta f/f]=\gamma\Delta Zs$. Measurement by this method is used even in the 100 GHz band. In this case, the resonator diameter is 4 mm, making it possible to measure small samples, and the measurement sensitivity is better to the extent of the higher frequency.

Within the scope of the BCS theory, the superconductor surface resistance at frequencies not higher than the energy gap frequency is known to increase in proportion to the square of the frequency. Thus in measuring the minute surface resistance of a superconducting material, the detection sensitivity increases with increasing frequency. Also as regards the anomalous skin effect in low-temperature metals, which is a highly interesting issue from the viewpoint of material physics, the higher the frequency is, the more advantageous it is for the measurement. Since the conventional hollow resonator is ordinarily used in fundamental mode or very low order mode, however, it becomes so small when used in the short millimeter band as to make it difficult to form a weak resonator coupling region and also difficult to realize a resonator with a high Q value.

Moreover, when extremely loose coupling is established in a millimeter band hollow resonator by means of minute holes, the transmission and absorption loss at the minute coupling hole region reaches a level that cannot be neglected, while, moreover, a complex temperature dependence is apt to develop. The estimation of the unloaded Q value by reduction from the Q value and transmittance T permissible in light of hollow resonator theory involves unpredictable error factors.

The open resonator using a spherical mirror is one type able to achieve a high Q value in the short millimeter band. FIG. 2 shows conventional reflection-type open resonators, each comprised of a spherical mirror 1, equipped with a waveguide coupling region, and a plane reflection mirror 2. FIG. 2(a) illustrates a reflection-type open resonator that uses a somewhat large coupling hole 4 at the coupling region between a waveguide 3 and the spherical reflection mirror 1. In this case, the decrease in the resonance mode exciting efficiency caused by the diffraction effect on the signal electromagnetic wave 5 radiated into the interior of the open resonator through the coupling hole 4 is not so serious, so that the reflected wave variation in the vicinity of resonance can be obtained at a S/N ratio required for reflection-type measurement. Since a rather large coupling hole 4 is provided at the center of the spherical reflection mirrors, however, the mirror surface reflectance is lowered, giving the open resonator a low Q value.

For detecting minute differences in surface reflection, however, it is necessary to use a measurement system based on a high Q value open resonator. FIG. 2(b) shows a configuration which obtains a high Q value by using a coupling hole 4' that is small relative to the wavelength of the signal electromagnetic wave. In this case, although the high surface reflectance of the spherical reflection mirror makes it possible to obtain a high Q value of 105 or higher, the signal electromagnetic wave 5' radiated into the interior of the open resonator through the coupling hole 4' is diffused into the internal space of the open resonator over a wide angle owing to the strong diffraction effect of the small opening. As a result, most of the signal electromagnetic wave 5' entering the interior of the open resonator through the small coupling hole 4' is lost to the outside of the open resonator and only a very small part of the whole signal electromagnetic wave 5' is effectively converted into the basic resonator mode 7 (TEMooq, where q is an integer indicating the vertical mode number) and stored in the resonator as energy. Since the reflected wave observed on the signal source side is, therefore, not sensitive to the resonant state inside the open resonator, this configuration is not practical as a reflection-type open resonator.

The inventors' research results demonstrate the possibility of a high-sensitivity, high Q value reflection-type open resonator enabling detection of variation in the internal loss of the open resonator (The 13th International Conference on IR & MM Waves, 1988, Honolulu, Hi., Conference Digest SPIE Vol. 1039, p199, 1988).

FIG. 3 shows the configuration of a reflection-type open resonator with the aforesaid high reflectivity and having a quasi-optical coupling region. It is configured as a half-symmetrical open resonator comprising a flat reflection mirror 2 and an opposing spherical reflection mirror 8, or something resembling the spherical reflection mirror 8, but having at the center of its mirror surface a high reflectance circular coupling region of an adequately large diameter relative to the wavelength. In this case, the spherical reflection mirror can be finished as a mirror with high reflectivity and a high Q value more than $10^5$ can easily be attained, while, at the same time, the weak diffraction effect at the large-diameter coupling region 9 makes it possible to hold down the conversion loss between the exiting beam 10 and the resonator mode 7. During resonance, the resonance dip caused by interference between the reflected wave 11 from the coupling region 9 and the signal wave 12 leaking from the quasi-optical coupling region 9 that is the part of the electromagnetic wave stored in the open resonator is observed with a substantial S/N ratio. The test reflection mirror specimen 2 is maintained in good thermal contact with the heat sink 13 and the temperature of the reflection mirror specimen 2 is set by controlling the temperature of the heat sink 13. When the temperature dependence of the surface reflectance characteristics of a metallic or superconducting material is measured, however, a problem arises owing to the fact that, in addition to the variation in the reflection characteristics of the flat mirror being tested, variation which directly affects the measurement Q value also occurs in the effective surface reflectance of the spherical reflectance mirror because of differences in the temperature of the spherical reflectance mirror, the measurement frequency and the vertical mode number of the resonance.

As explained in the foregoing, in the conventionally used measurement methods, the surface loss of the test specimen has been calculated from the difference in reflection characteristics relative to a reference reflection mirror specimen, by approximation using numerical analysis or by unloaded Q value estimation involving many error factors. Thus the inability to directly extract and measure the effect of losses included in the experimentally determined resonator Q value owing to causes other than the test specimen has made it impossible to accurately obtain the desired reflection loss at the test specimen surface by conversion.

The prior art technologies described above are near their measurement technology resolution limit in areas such as research into high-reflectance thin metal film surfaces (where the fact that the mean free path is larger than the classical skin depth makes the anomalous skin effect a problem) and such as the more recent evaluation of the surface impedance characteristics of superconducting thin film materials (which is improving in quality). A need has, therefore, arisen for a new high-precision technology capable of measuring surface impedance in the millimeter to sub-millimeter wave region with high-sensitivity and accuracy.

SUMMARY OF THE INVENTION

This invention was accomplished in light of the aforesaid circumstances and has as its object to provide a method and apparatus for measuring the surface characteristics of a material, more particularly to provide such a method and apparatus wherein minute reflection loss and very minute variation in reflectivity of a high-reflectance mirror material with respect to high-frequency electromagnetic fields in the microwave—sub-millimeter wave region are detected at high sensitivity and the result is used for, in the case of a metal, calculating the effective skin depth and, in general, calculating the surface impedance, including the reflectivity and phase.

For achieving this object, the invention measures the surface characteristics of a material with respect to a high-frequency electromagnetic field by placing opposite a flat mirror material to be tested one of a pair of concave spherical reflection mirrors having same-diameter circular mirror surface openings and the same radii of curvature, being formed at the center of the mirror surfaces with circular coupling regions constituting partially transmissive reflection mirror surfaces of the same pattern and area and having mirror surfaces and mirror surface substrates of entirely the same materials, placing the other spherical reflection mirror at a position symmetrical to the one reflection mirror with respect to the flat mirror material as the plane of symmetry for use in calibrating mirror surface reflection loss, measuring the Q value of the open resonator formed by the one reflection mirror and the flat mirror material, removing the flat mirror material from the optical axis, measuring the Q value of the open resonator formed by the pair of spherical reflection mirrors, calculating the absolute value of the reflectance of the flat mirror material to be tested from the difference between the two measured Q values, and calculating the phase of the reflected wave at the surface of the flat mirror material to be tested from the measured resonance position, thereby determining the surface characteristics of the material with respect to a high-frequency electromagnetic field.

The above and other objects and features of the invention will be better understood from the following description made with respect to the drawings.

DETAILED DESCRIPTION OF THE PREFERRED EMBODIMENT

Figure 1A:
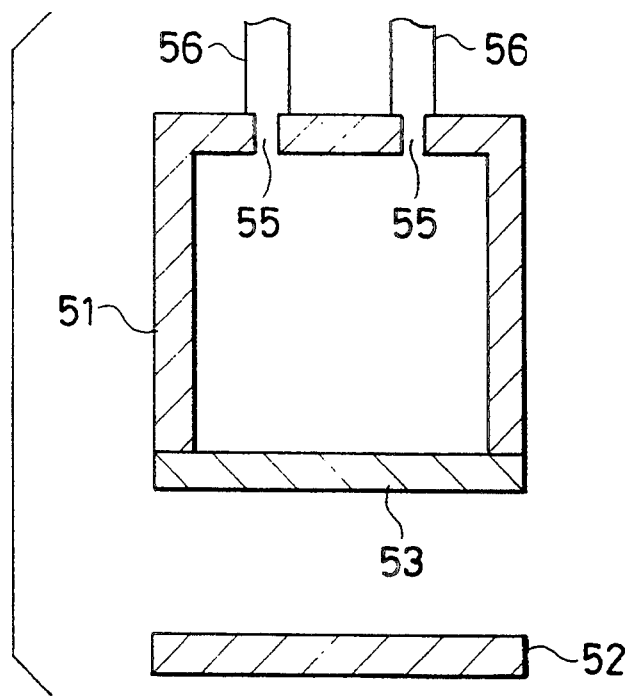
FIG. 1(a) is a schematic view of a prior-art transmission-type hollow cylindrical resonator for measuring the surface impedance of a high-temperature superconductor.
Figure 1B:
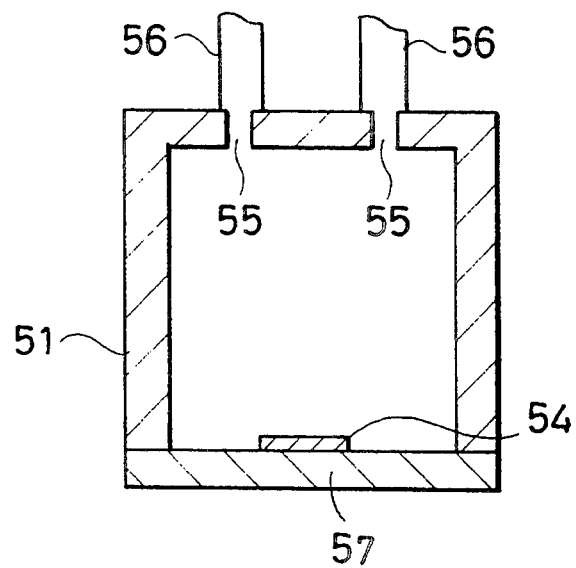
FIG. 1(b) is a schematic view of another prior art hollow cylindrical resonator.
Figure 2A:
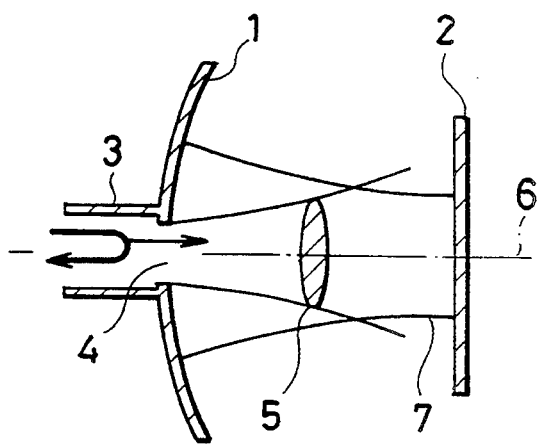
FIG. 2(a) is a schematic view of a prior-art reflection-type open resonator having a coupling region with a somewhat large coupling hole.
Figure 2B:
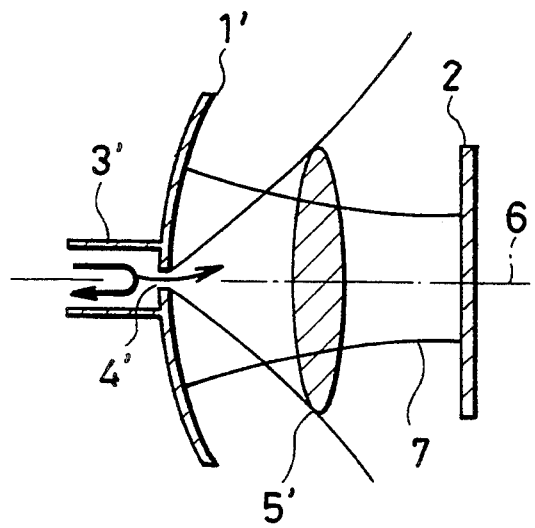
FIG. 2(b) is a schematic view of a prior-art reflection-type open resonator having a coupling region with a coupling hole that is small relative to the wavelength of the electromagnetic wave.
Figure 3:
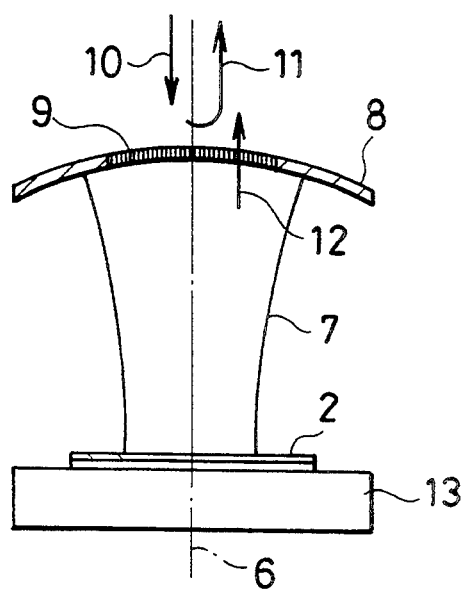
FIG. 3 is a schematic view of a prior-art reflection-type open resonator using a spherical reflection mirror provided with a high-reflectance quasi-optical circular coupling region.

The diagrams of FIG. 4 are for explaining the principle of the method for measuring the surface characteristics of a material according to the invention. For enabling calibration of surface reflection loss with small error over the wide temperature range, there is used a pair of concave spherical reflection mirrors 14, 15 which have the same radii of curvature and the same diameter mirror surface openings, are formed at the center of the mirror surfaces with circular coupling regions constituting partially transmissive reflection mirror surfaces of the same pattern, position and area, and have mirror surfaces and mirror surface substrates of entirely the same materials. The aforesaid circular coupling region 9 at the centers of the pair of concave spherical reflection mirror surfaces 14 and 15 are high-reflectance partially transmissive reflection mirror surfaces configured as a periodic structure whose periodicity is much smaller than the wavelength.

The circular coupling regions 9 formed at the centers of the concave spherical reflection mirrors 14, 15 will now be explained in detail.

Since the distribution of the electromagnetic field on the mirror surface of the spherical reflection mirror is determined by the radius of curvature of the spherical reflection mirrors and the distance between the two spherical reflection mirrors, appropriate selection of the diameter of the mirror surface openings makes it possible in actual practice to ignore the energy leaking out from the periphery of the reflection mirror surface during repeated reflection between the spherical reflection mirrors. In such a case, with an open resonator constituted of spherical reflection mirrors, the Q value of the resonator is determined by the reflection loss of the mirror surfaces. Therefore, (1) if a high-reflectance partially transmissive coupling region is provided at the center of each concave spherical reflection mirror (which has a focusing, effect), a high Q value can be secured, and (2) if the coupling region is provided to about the extent of the beam spot on the spherical reflection surface, the coupling region will be larger than the wavelength so that a high mode-exciting efficiency can be obtained by feeding with a signal beam close to the mode inside the resonator.

For actually obtaining a reflection mirror surface with high mirror surface precision and high quality, there is used an optically polished sapphire, quartz or other such spherical mirror substrate transparent to millimeter waves and sub-millimeter waves, and a reflection mirror surface is formed on the surface thereof as a metal thin film or a superconductor thin film. The circular coupling region 9 at the center of the spherical reflection mirror is formed with fine pattern features of periodically repeating portions covered with metal thin film or superconductor thin film and portions where the substrate is exposed, whereby making use of the effect of the partial leakage of electromagnetic wave energy at the gaps between the portions covered by the conductor film, a high-reflectance partially transmissive coupling region is obtained. By adjusting the size of the fine pattern features relative to the wavelength to within the range of 1/40–1/1000 the wavelength of the electromagnetic wave, it is possible to select the high reflectance of the coupling region, while the use of patterned thin film makes it possible to reduce greatly the transmission absorption loss of the transmitted component from the high-reflectance mirror surface. The pattern of the coupling region can be any of various types, such as parallel stripes, orthogonal lattice or the like. Since highly advanced thin film processing and fine processing technologies can be used to form and process these thin film patterns on the mirror surface, it is possible to form the coupling region to a high degree of fabrication precision relative to millimeter—sub-millimeter waves of 100–600 GHz.

From the point of realizing a high Q value it is advantageous to use a thin film material with low surface reflection loss as the mirror surface material of the spherical reflection mirrors 14, 15 and their coupling regions 9. In particular, it is known that the electric conductivity of metal materials such as high purity copper, gold and silver differs by several orders of magnitude between room temperature and the temperature of helium, making the selection of the mirror surface material important for use in measuring minute surface loss characteristics over a broad temperature range. By holding spherical reflection mirrors comprising high-purity metal mirror surfaces at a low temperature it is possible to realize a high-sensitivity characteristic measurement apparatus with a Q value 100 times that at room temperature. Further, since a high quality superconducting thin film material is of itself low in surface reflection loss, spherical reflection mirrors using high quality superconducting thin films are appropriate for the measurement and evaluation thereof.

Figure 4A:
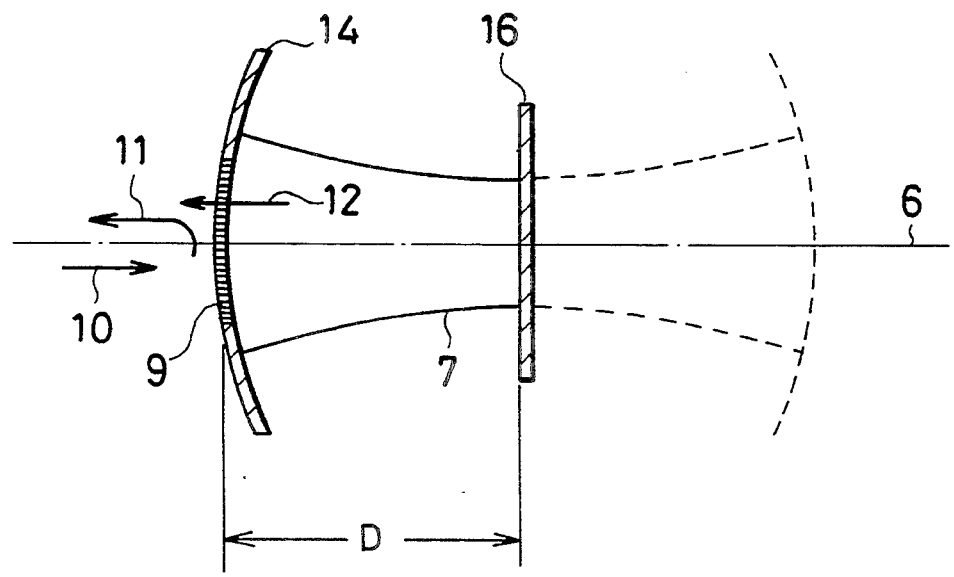
FIG. 4(a) is an explanatory view of a half-symmetrical open resonator constituted of a spherical reflection mirror and a flat mirror to be tested, in the method for measuring the surface characteristics of a material according to the invention.
Figure 4B:
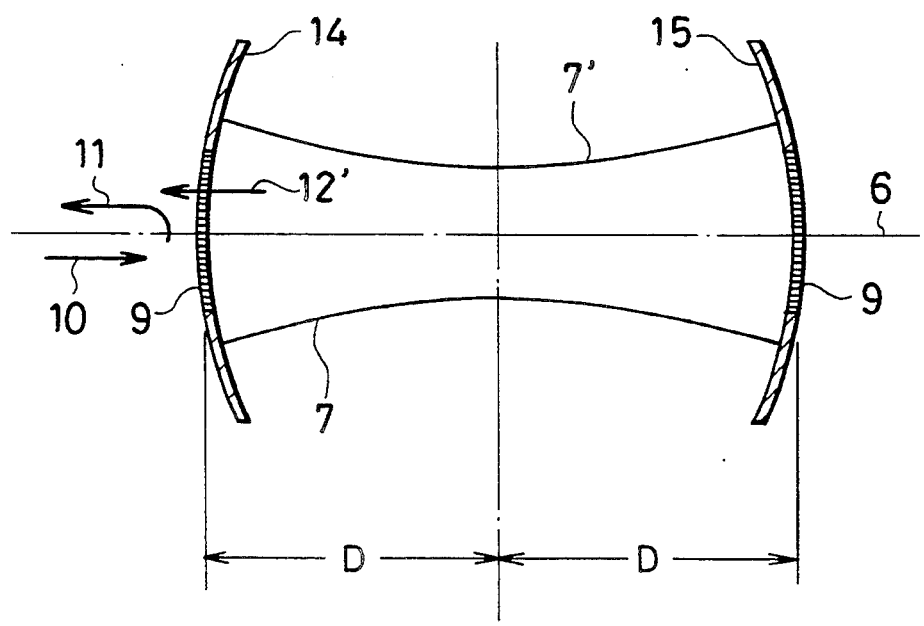
FIG. 4(b) is an explanatory view of a symmetrical open resonator constituted of a pair of identical spherical reflection mirrors.

Of the pair of concave spherical reflection mirrors mentioned above, one reflection mirror 14 is used as the main reflection mirror, and the configuration of a reflection-type open resonator wherein it is placed opposite the flat mirror material 16 to be tested is shown in FIG. 4(a). On the other hand, FIG. 4(b) shows a reflection-type open resonator configured by removing the flat mirror material 16 to be tested and placing the other spherical reflection mirror 15, which is fabricated to be the same as the reflection mirror 14, at a position symmetrical to the main reflection mirror 15 with respect to the flat mirror material 16. In this case, the opening diameters of the pair of spherical reflection mirrors 14, 15 and the flat mirror material 16 are selected to be about 4–6 times the size of the beam spot at the mirror surfaces, and the part of the electromagnetic wave energy stored between the mirror surfaces in Gaussian beam TEMooq mode 7 which spills from the periphery of the reflection mirror surfaces as loss, specifically the diffraction loss, is extremely small and is set to be negligible in comparison with other losses.

The Q value of the resonator, which is the product of the electromagnetic frequency $\omega$ and the quotient obtained by dividing the energy U stored in the mode by the loss per unit time -dU/dt, is given by $$Q = \omega \frac{U}{-\frac{dU}{dt}} \quad (1)$$

Defining the distance between the spherical reflection mirror 14 and the flat mirror material 16 as D and the rate of loss during each passage back and forth over this distance as L, the loss per unit time is $$\frac{dU}{dt} = -\frac{coL}{2nD} u \quad (2)$$

where co is the speed of light in a vacuum and n is the index of refraction of the medium inside the open resonator. Using Equation (2) to rewrite Equation (1), gives Equation (3):

$$Q = \frac{2nD}{co} \cdot \frac{\omega}{L} \quad (3)$$

The total loss rate L of the open resonator of FIG. 4(a) is the sum of the loss rate LM1 of the reflection at the spherical reflection mirror 14, the loss rate LS of the reflection at the flat mirror material 16 and the loss rate LD owing to the diffraction effect. If the diffraction loss is treated as negligible so that LD=0, the Q value Qm of the resonator of FIG. 4(a) is given by the following equation.

$$Qm = \frac{2nD}{co} \cdot \frac{\omega}{LM1 + LS} \quad (4)$$

The configuration obtained when the flat mirror material 16 is then removed and the spherical reflection mirror 15 fabricated to be the same as the reflection mirror 14 is positioned on the same optical axis 6 at a distance of 2D from the spherical reflection mirror 14 is the open resonator of FIG. 4(b). In this case, the resonant mode of FIG. 4(b) is a symmetrical double mode (7+7'), as against the half-symmetrical mode 7 in the case of FIG. 4(a), and the size of the beam spot on the mirror surface of the spherical reflection mirror 14 remains unchanged in both FIGS. 4(a) and (b) and is the same as that on the mirror surface of the spherical reflection mirror 15. Defining the Q value of the resonator of FIG. 4(b) as QM and the resonator length as 2D, the loss rate LM2 of the reflection at the spherical reflection mirror 15 becomes as shown by Equation (5).

$$QM = \frac{4nD}{co} \cdot \frac{\omega}{LM1 + LM2} \quad (5)$$

The latest thin film technology, which has high controllability, can be used in fabricating the spherical reflection mirrors 14, 15, enabling them to be made so that their loss rates LM1 and LM2 are the same. For dealing with these generally, inclusive of minute characteristic differences, it is possible to use a small coefficient $\alpha$ to set out the loss rate LM2 as in Equation (6).

$$LM2 = (1+\alpha) LM1 \quad (6)$$

From Equations (4), (5) and (6), the reflection loss rate LS at the flat mirror material 16 becomes $$LS = \frac{2nD\omega}{co} \left( \frac{1}{Qm} - \frac{1}{(1 + \alpha/2) QM} \right) \approx \quad (7)$$

$$\frac{2nD\omega}{co} \left( \frac{1}{Qm} - \frac{1 - \alpha/2}{QM} \right)$$

By using the relationship of Equation (7) it is therefore possible to obtain the absolute value of the loss rate LS of the mirror reflection of the flat mirror material 16 from the Q value (Qm) of the open resonator of the configuration of FIG. 4(a) and the Q value (QM) of the open resonator of the configuration of FIG. 4(b).

When there is no difference between the loss rates LM1 and LM2 of the spherical reflection mirrors 14, 15, i.e. When $\alpha=0$, Equation (7)' holds.

$$LS = \frac{2nD\omega}{co} \left( \frac{1}{Qm} - \frac{1}{QM} \right) \quad (7)'$$

The reflection coefficient $\Gamma$ can be expressed as a complex number including the phase $\theta$ in the amplitude $|\Gamma|$ $$\Gamma = |\Gamma| \exp j\theta = u + jv \quad (8)$$

Since the amplitude of the reflected wave is not larger than that of the incident wave, $|\Gamma| \leq 1$, the reflection coefficient $\Gamma$ appearing in Equation (8) thus represents a point on the unit circumference or a point within the unit circle on the complex plane. The relation of the reflection coefficient $\Gamma$ to the surface impedance ZS and the free space impedance Z0 ($\sim 377 \Omega$) of a flat mirror in free space is expressed by $$\Gamma = \frac{ZS - Z0}{ZS + Z0} \quad (9)$$

or $$\frac{ZS}{Z0} = \frac{1 + \Gamma}{1 - \Gamma} \quad (10)$$

Defining the surface impedance ZS as $$ZS = R + jX \quad (11)$$

and substituting Equations (8) and (11) into Equation (10) gives $$R + jX = Z0 \frac{1 + u + jv}{1 - u - jv} \quad (12)$$

Assuming equality between the real number portions and imaginary number portions respectively, we get $$\frac{R}{Z0} = \frac{(1 - u^2) - v^2}{(1 - u)^2 + v^2} \quad (13)$$

$$\frac{X}{Z0} = \frac{2v}{(1 - u)^2 + v^2} \quad (14)$$

Since the power reflectivity is $|\Gamma|^2$, the loss rate LS of the reflection at the flat reflection mirror stands in the following relationship:

$$LS = 1 - |\Gamma|^2 \quad (15)$$

The absolute value $|\Gamma|$ of the reflection coefficient can, therefore, be found using the measured Q values of the open resonators of the configurations of FIGS. 4(a) and 4(b) and the Equations (7) and (15).

Moreover, in the open resonator of the configuration of FIG. 4(a), when the phase angle $\theta$ of the reflection coefficient $\Gamma$ is such that $\theta \neq (2n-1)\pi$ (n being an integer), the minimum electric field point of the standing wave is shifted off the mirror surface of the flat mirror material 16. If the shift in the resonance point between the resonator length D during measurement of the flat mirror material 16 and the resonator length D0 in the case where it is a metal mirror surface of high conductivity such that $\theta = \pm \pi$ in the same vertical mode number q is defined as d, i.e. if $d = D0 - D$, then, using the wavelength $\lambda$ of the electromagnetic wave, the phase angle $\theta$ of the reflection coefficient $\Gamma$ of the flat mirror material 16 is given by $$\theta = \pi \left( 1 - \frac{4d}{\lambda} \right) \quad (16)$$

Here, $2\pi/\lambda = n\omega/co$.

The surface impedance ZS of a normal metal is given in the ZS expressed by Equation (11), by $$R = X = (\omega\mu 0/2\sigma)^{\frac{1}{2}} \quad (17)$$

where $\mu 0$ is the permeability of a vacuum and $\sigma$ is the conductivity of the metal. In the case of reflection at a metal surface having a high conductivity $\sigma$, it holds that $|ZS/Z0| \ll 1$, so that in a good approximation the power reflectance is $$|\Gamma|^2 \approx 1 - \frac{4R}{Z0} \quad (18)$$

Using the loss rate LS of the mirror surface reflection at the flat mirror material 16 obtained from Equation (7), the surface resistance R of the flat mirror material 16 is obtained from the relationships of Equations (15) and (18) as $$R = \frac{Z0}{4} LS \quad (19)$$

On the other hand, when a high-frequency electromagnetic wave is applied to a good conductor such as a metal, a large conduction current many times larger than the displacement current causes the wave number k to become a complex number $k = (-j\omega\sigma\mu 0)^{\frac{1}{2}}$ and the traveling wave attenuates exponentially in the depth direction from the surface. The attenuation length at this time is referred to as the skin depth $\delta$ and is given by $$\delta = (2/\omega\sigma\mu 0)^{\frac{1}{2}} \quad (20)$$

In light of Equations (17) and (20), the relationship between the surface resistance R and skin depth $\delta$ is $$R = \omega\mu 0\, \delta/2 \quad (21)$$

From the fact that the free space impedance Z0 is $Z0 = 1\epsilon 0 c = \mu 0 c$ and in light of Equations (19) and (20), the experimentally obtained loss rate Ls of the mirror surface reflection at the flat mirror material 16 can be used to obtain the effective value of the skin depth $\delta$ as $$\delta = (c0/2\omega)\, Ls, \quad (22)$$

or, using Equation (7) as $$\approx nD \left\{ \frac{1}{Qm} - \frac{1 - \alpha/2}{QM} \right\} \quad (22')$$

On the other hand, when it holds that $|ZS/Z0| \gg 1$, as in the case of a magnetic wall, the equation approximating the power reflectivity is $$|\Gamma|^2 \approx 1 - \frac{4Z0}{|ZS|} \quad (23)$$

Using the mirror reflection loss rate LS, the surface impedance ZS of the flat mirror material 16 is given by (24).

$$|ZS| = \frac{4Z0}{LS} \quad (24)$$

As explained in the foregoing, by using a high Q value open resonator, the method of the present invention for measuring the surface characteristics of a material with respect to a high-frequency electromagnetic wave not only enables the minute high-frequency wave loss occurring at the surface of a high-conductivity metal thin film or a superconductor, and minute changes therein, to be detected at a higher sensitivity than by conventional methods but also enables high-precision measurement of the absolute value and phase component of the minute high-frequency loss of the mirror surface material being tested.

Figure 5:
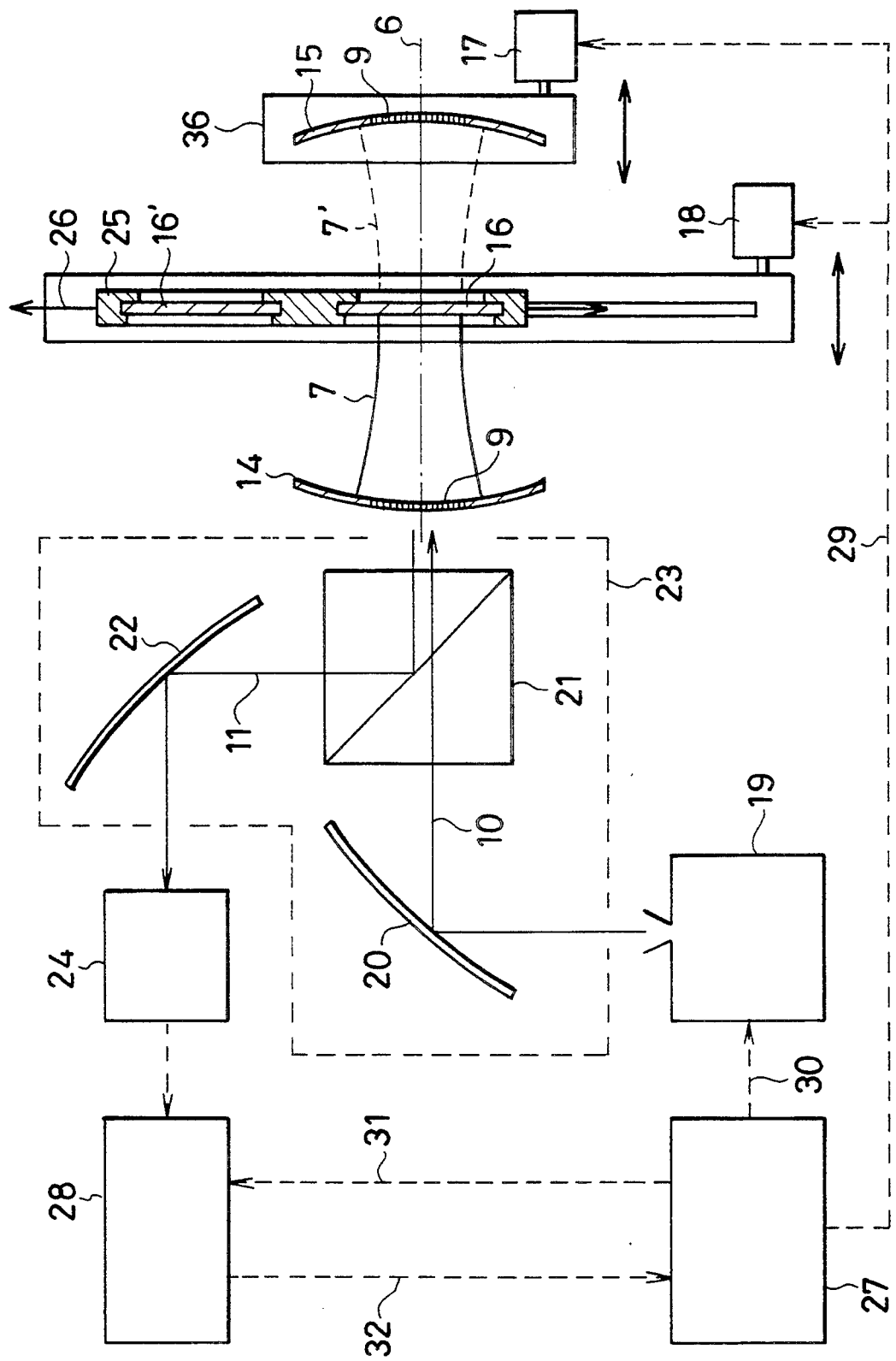
FIG. 5 is a configurational view of an embodiment of an apparatus for measuring the surface characteristics of a material according to the invention.

FIG. 5 shows the configuration of an apparatus according to the invention for measuring the surface characteristics of a material with respect to a high-frequency wave. In this apparatus for measuring the surface characteristics of a material, a pair of concave spherical reflection mirrors 14, 15 made from the same materials in exactly the same way are disposed facing each other to configure a resonator. One reflection mirror 15 is mounted on a holder 36 and is driven back and forth, as shown by arrows, by a drive mechanism 17 to adjust its distance from the spherical reflection mirror 14. A transfer carriage 26 carrying a material holder 25 is mounted between the aforesaid pair of reflection mirrors 14, 15 of the resonator for positioning a specimen flat mirror material 16 on the optical axis of the resonator. The transfer carriage 26 is moved back and forth, as shown by arrows, by a drive mechanism 18 driven by a mirror surface position control signal 29 from a measurement control computer 27, whereby the mirror-to-mirror distance between the spherical reflection mirror 14 and the flat mirror material 16 is set so as to obtain the prescribed resonator frequency. As the high-stability sweep signal source 19 for exciting and conducting precision measurement with the resonator formed in this way by the reflection mirror 14 and the flat mirror 16 there can be used a Gunn oscillator (whose frequency band can be selectively set between 100 and 120 GHz) phase-locked with a high-stability crystal reference frequency generator, and by controlling the frequency of a microwave band synthesizer using a frequency control signal 30 from the measurement control computer 27, approximately 100 MHz sweep at step intervals of 10 Hz or more can be achieved. An exciting signal 10 leaving the signal source 19 passes through a beam guide system 23 comprising beam condenser reflection mirrors 20, 22 and a circulator 21 and enters the resonator through the coupling region 9 of the concave spherical reflection mirror 14. A reflected wave 11 is separated at the circulator 21 and sent to a signal detector 24 by the beam condenser reflection mirror 22. After photoelectric conversion at the signal detector 24, the signal is sent to a signal processor 28 controlled by a data control signal 31.

In actual measurement, first the frequency is swept in 100–200 KHz steps by the frequency control signal from the measurement control computer 27 to find the resonant point. Next, for conducting the measurement with high resolution, the frequency is swept in 10–40 KHz steps and the resonance dip signal is recorded by the signal processor 28. This measures the Q value Qm corresponding to the spherical reflection mirror 14 and the specimen flat reflection material 16 and represented by Equation (4). Next, the specimen flat mirror material 16 set in the material holder 25 is removed from the optical axis 6 by an appropriate means, and the drive mechanism 17 is driven by the mirror position control signal 29 from the measurement control computer 27 to move the holder 36 for transferring the spherical reflection mirror 15 to a position on the same optical axis 6 that is separated from the spherical reflection mirror 14 by twice the interval of the specimen flat mirror material 16 therefrom. This operation forms a symmetrical double mode (7+7'), as against the half-symmetrical mode 7.

In this state, by measuring the resonance characteristics by sweeping the frequency in exactly the same way as described earlier, the Q value QM given by Equation (5) for the resonator constituted by the spherical reflection mirrors 14, 15 can be obtained. If the data signal 32 is used in Equations (19), (22) and (24), the skin depth and surface impedance can be obtained as surface characteristics of the specimen flat mirror material 16 with respect to a high-frequency electromagnetic field. Further, by placing another flat mirror material 16' in the holder 25, using the transfer carriage 26 to shift the material 16' into the position of the material 16, using the drive mechanism to move the material 16' back and forth under the same conditions, and finding its resonance position at the same frequency as in the case of material 16, the phase angle $\theta$ can be accurately obtained from the relationship between the travel distance and the wavelength.

Figure 6:
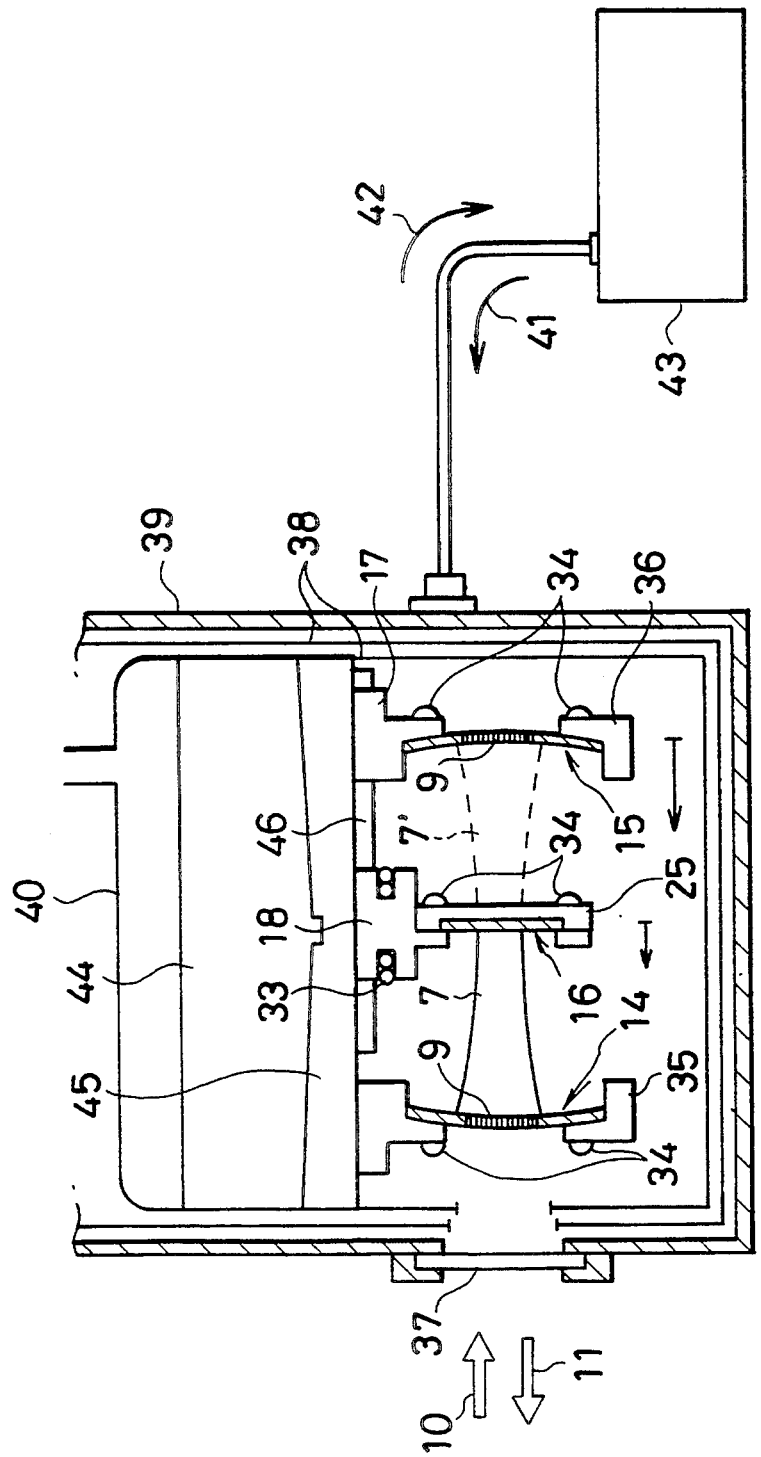
FIG. 6 is a configurational view of another embodiment of an apparatus for measuring the surface characteristics of a material according to the invention.

FIG. 6 shows another embodiment of the apparatus according to the invention for measuring the surface characteristics of a material. In this embodiment, for measuring the temperature dependence of surface reflection characteristics with regard to a mirror surface material, the pair of spherical reflection mirrors 14, 15 constituting the open resonator shown in FIG. 4 and the flat mirror material interposed between them are held by holders 35, 36, and 25, respectively, so as to be positioned inside a vacuum vessel 39 which has its interior enclosed by heat shield plates 38 and is equipped with a vacuum window 37. A coolant reservoir 40 containing coolant 44 is provided inside the aforesaid vacuum vessel 39. The holder 25 of the flat mirror material 16 is suspended so as to enable heat transfer with a heat sink 45 provided on the bottom surface of the coolant reservoir 40 and to be movable along a rail 46 by a drive mechanism 18 for adjusting the mirror interval. It is further equipped with a heater 33 and a temperature sensor 34 and provided with the capability to set and control the temperature of the aforesaid flat mirror material 16 within the range of 4.2–300K by controlling the heater current 41 relative to the temperature signal 42 from the temperature sensor 34. Also, for preventing a temperature difference from arising between the opposing pair of reflection spherical mirrors 14, 15, the arrangement provides sufficient thermal contact between the spherical mirror holders 35, 36 and the heat sink 45.

The holder 35 of the spherical reflection mirror 14 is of the fixed type in this embodiment and is in direct thermal contact with the heat sink 45. The holder 36 of the spherical reflection mirror 15 has a drive mechanism 17 for setting the mirror interval and is constituted to be slidable along the rail 46. As one method for securing heat transfer at the movable portions of these members, the aforesaid holders 36, 25 are thermally contacted with the heat sink by flexible gold-plated thin copper sheet laminates.

As the coolant 44 in the coolant reservoir 40, either liquid nitrogen or liquid helium can be used as required. While use of a coolant is indicated in this embodiment, it can be replaced by temperature control with a refrigerator system.

In the measurement of material properties using a resonator, the resolution characteristics generally increase with an increasing Q value. In the case where a thin metallic film of gold or copper is used for the mirror surfaces of the spherical mirrors, resonator Q values at room temperature of 100,000–300,000 are currently obtained, making use as a reflection-type open resonator possible. When a superconductor is used as the spherical reflection mirror surface material in place of gold or copper thin film, a Q value higher by 1–3 orders of ten can be anticipated, which, together with the ability to maintain an adequately low temperature relative to the superconductivity transition temperature, enables realization of a system able to detect very weak phenomenon with even higher sensitivity.

In the open resonator configuration of FIG. 4(b) using the pair of spherical reflection mirrors 14, 15, the securement of high symmetry is important to high-precision measurement. Changes in the measurement frequency and resonation vertical mode number may produce a slight change in the size of the beam spot on the spherical reflection mirror surfaces 14, 15 and, in addition, since the coupling efficiency of leaking from the electromagnetic wave coupling regions 9 of the spherical reflection mirrors 114, 15 depends on changes in these (temperature, vertical mode number, wavelength), they subtly change the mirror surface reflectance. Further, in measurement entailing temperature change, since the reflectance of the spherical reflection mirrors themselves are inherently temperature dependent, it is important to measure and extract the losses of the spherical reflection mirrors as they are, without changing the temperature, vertical wave number or wavelength. As set out in the foregoing, in accordance with this invention, it is possible at the individual measurement temperatures to measure and extract the reflection losses at the spherical reflection mirrors under the same measurement frequency and vertical mode number conditions. Particularly in the measurement of the surface impedance of a superconductor or the like and in the measurement of the anomalous skin effect of a low-temperature metal, which inherently require measurement with a resonator over a broad temperature range, it becomes possible to accurately calibrate the absolute value of extremely small reflection losses. Further, the invention for the first time makes possible high-precision measurement of the surface impedance of a material in the millimeter—sub-millimeter wave band, which has not been feasible up to now.

Measurement of the surface impedance of superconducting thin film materials, the next generation of ultra-high speed electronic materials, is of great significance. By using a superconducting thin film, high-conductivity metallic thin film or other such high-reflectance mirror surface material as the flat reflection mirror on one side of a Fabry-Perot resonator, the present invention makes it possible to precisely measure the minute surface losses of these materials over a broad range of temperatures, between the temperature of liquid helium and room temperature, and enables absolute calibration of 1/1000–2/1000 surface reflectance losses at a precision of several percent. The reflectance loss measurement limit at room temperature and 100 GHz using a copper thin film mirror surface is just under 2 m$\Omega$, with 0.6–0.7 m$\Omega$ probably attainable at the temperature of liquid nitrogen, which is a sensitivity at least one order of ten higher than what has heretofore been reported for the measurement of the surface loss of a high-temperature superconductor. It is the system for precision measurement of high-frequency wave surface loss having the highest frequency and the highest Q value. Moreover, the invention is superior to other measurement methods in the point that it determines the loss at the material surface being measured after directly measuring the losses other than that of the mirror surface material being measured. It was confirmed that the measurement of material surface characteristics using a high Q value reflection-type open resonator according to the invention constitutes an important, highly effective, new measurement method which can be used in furthering research into the anomalous skin effect of low-temperature metals and research and development of high-temperature superconducting materials for use at high-frequency, and the like. If technology for using high-temperature superconducting thin-film for spherical reflection mirror surfaces can be developed, it would have high technological utility in enabling ready achievement of measurement systems with heretofore unheard-of ultra-high Q values.

What is claimed is:

1. A method for measuring the surface characteristics of a material with respect to a high frequency electromagnetic field comprising: forming a reflection-type open resonator by placing opposite a flat mirror material to be tested one of a pair of spherical reflection mirrors being concave and having same-diameter circular mirror surface openings and the same radii of curvature, the surface openings being formed at the center of the pair of spherical reflection mirrors with circular coupling regions constituting partially transmissive reflection mirror surfaces of the same pattern and area, the spherical reflection mirrors having mirror surfaces and mirror surface substrates of entirely the same materials; placing the other of the pair of spherical reflection mirrors at a position symmetrical to said one of the pair of spherical reflection mirrors with respect to the flat mirror material as the plane of symmetry for use in calibrating mirror surface reflection loss; measuring the Q value of an open resonator formed by said one of the pair of spherical reflection mirrors and the flat mirror material; removing the flat mirror material from the optical axis; measuring the Q value of an open resonator formed by the pair of spherical reflection mirrors; calculating the absolute value of the reflectance of the flat mirror material to be tested from the difference between the two measured Q values; and calculating the phase of the reflected wave at the surface of the flat mirror material to be tested from the measured resonance position; thereby determining the surface characteristics of the material with respect to a high-frequency electromagnetic field.

2. A method for measuring the surface characteristics of a material according to claim 1, further comprising: independently using under the same conditions two different flat mirror materials to be tested to configure resonators with said one of the pair of reflection mirrors and obtaining the phase angle from the resonance lengths and the signal wavelength.

3. An apparatus for measuring the surface characteristics of a material with respect to a high-frequency electromagnetic field comprising: a pair of concave spherical reflection mirrors having same-diameter circular mirror surface openings and the same radii of curvature, being formed at the center of the mirror surfaces with circular coupling regions constituting partially transmissive reflection mirror surfaces of the same pattern and area, having mirror surfaces and mirror surface substrates of entirely the same materials, and being disposed in facing relationship across a prescribed interval to constitute a resonator;

a reflection mirror movement means for adjusting the interval between the concave spherical reflection mirrors;

a flat mirror to be tested disposed on an optical axis between the pair of reflection mirrors to constitute with one of the pair of reflection mirrors a resonator having half the interval of the aforesaid resonator;

means for removing the flat mirror material from the optical axis;

signal supply means for exciting the resonators; and signal processing means for detecting and processing reflection signals from the resonators.

4. An apparatus for measuring the surface characteristics of a material according to claim 3, wherein the circular coupling regions constituting reflection mirror surfaces are configured as fine pattern features of periodically repeating portions covered with metal thin film and portions where the substrate is exposed.

5. An apparatus for measuring the surface characteristics of a material according to claim 3, wherein the circular coupling regions constituting reflection mirror surfaces are configured as fine pattern features of periodically repeating portions covered with superconductor thin film and portions where the substrate is exposed.

6. An apparatus for measuring the surface characteristics of a material according to claim 4, wherein the size of the pattern features is 1/40–1/1000 the wavelength of the electromagnetic wave.

7. An apparatus for measuring the surface characteristics of a material according to claim 5, wherein the size of the pattern features is 1/40–1/1000 the wavelength of the electromagnetic wave.

8. An apparatus for measuring the surface characteristics of a material according to claim 3, further comprising means for maintaining the temperature of the flat mirror material in the range of 4.2–300K.

9. An apparatus for measuring the surface characteristics of a material according to claim 3, further comprising means for maintaining the pair of facing spherical reflection mirrors at the same temperature.

* * * * *